(12) United States Patent
Chen et al.

(10) Patent No.: US 8,901,452 B2
(45) Date of Patent: Dec. 2, 2014

(54) MULTIPLE BEAM LASER SYSTEM FOR FORMING STENTS

(71) Applicant: Abbott Cardiovascular Systems Inc., Santa Clara, CA (US)

(72) Inventors: Li Chen, San Jose, CA (US); Randolf Von Oepen, Los Altos, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 40 days.

(21) Appl. No.: 13/914,524

(22) Filed: Jun. 10, 2013

(65) Prior Publication Data

US 2013/0313237 A1  Nov. 28, 2013

Related U.S. Application Data

(62) Division of application No. 12/699,391, filed on Feb. 3, 2010, now Pat. No. 8,461,478.

(60) Provisional application No. 61/149,621, filed on Feb. 3, 2009, provisional application No. 61/149,645, filed on Feb. 3, 2009.

(51) Int. Cl.
| | |
|---|---|
| *B23K 26/00* | (2014.01) |
| *A61M 25/00* | (2006.01) |
| *A61F 2/915* | (2013.01) |
| *A61F 2/91* | (2013.01) |
| *A61F 2/90* | (2013.01) |
| *B23K 26/38* | (2014.01) |
| *B23K 26/36* | (2014.01) |

(52) U.S. Cl.
CPC ............ *A61M 25/0013* (2013.01); *A61F 2/915* (2013.01); *A61F 2/91* (2013.01); *A61F 2/90* (2013.01); *B23K 26/38* (2013.01); *B23K 26/365* (2013.01)

USPC ............. 219/121.6; 219/121.68; 219/121.72; 219/121.76; 623/1.15; 623/1.34

(58) Field of Classification Search
CPC ........ B23K 26/38; B23K 26/385; A61F 2/91; A61F 2/915; A61F 2/90; A61F 2250/0085; A61F 2250/0086
USPC ............... 219/121.6, 121.68, 121.72, 121.76; 623/1.15, 1.34
See application file for complete search history.

(56) References Cited

U.S. PATENT DOCUMENTS

| | | | |
|---|---|---|---|
| 4,387,952 A | 6/1983 | Slusher | |
| 4,694,139 A | 9/1987 | Roder | |

(Continued)

FOREIGN PATENT DOCUMENTS

| | | |
|---|---|---|
| EP | 0 221 570 A2 | 5/1987 |
| EP | 0 364 787 A1 | 4/1990 |

(Continued)

OTHER PUBLICATIONS

International Search Report issued by European Patent Office on Jul. 8, 2010.

(Continued)

*Primary Examiner* — Michael Trinh
(74) *Attorney, Agent, or Firm* — Fulwider Patton LLP

(57) ABSTRACT

A system and method for precision cutting using multiple laser beams is described, The system and method includes a combination of optical components that split the output of a single laser into multiple beams, with the power, polarization status and spot size of each split beam being individually controllable, while providing a circularly polarized beam at the surface of a work piece to be cut by the laser beam. A system and method for tracking manufacture of individual stents is also provided.

6 Claims, 11 Drawing Sheets

(56) References Cited

U.S. PATENT DOCUMENTS

| | | |
|---|---|---|
| 4,697,087 A | 9/1987 | Wu et al. |
| 4,729,766 A | 3/1988 | Bergentz et al. |
| 4,733,665 A | 3/1988 | Palmaz |
| 4,736,381 A | 4/1988 | Eden et al. |
| 4,893,972 A | 1/1990 | Blaho |
| 4,947,022 A | 8/1990 | Ostroff et al. |
| 4,962,318 A | 10/1990 | Nishi et al. |
| 4,963,022 A | 10/1990 | Sommargren |
| 4,994,071 A | 2/1991 | MacGregor |
| 5,049,723 A | 9/1991 | MacDonald |
| 5,059,211 A | 10/1991 | Stack et al. |
| 5,064,537 A | 11/1991 | Chupka et al. |
| 5,073,694 A | 12/1991 | Tessier et al. |
| 5,102,417 A | 4/1992 | Palmaz et al. |
| 5,160,823 A | 11/1992 | Bennin et al. |
| 5,169,678 A | 12/1992 | Cole et al. |
| 5,222,617 A | 6/1993 | Gregory et al. |
| 5,306,286 A | 4/1994 | Stack et al. |
| 5,345,057 A | 9/1994 | Muller |
| 5,356,423 A | 10/1994 | Tihon et al. |
| 5,421,955 A | 6/1995 | Lau et al. |
| 5,514,154 A | 5/1996 | Lau et al. |
| 5,521,374 A | 5/1996 | Cray et al. |
| 5,569,295 A | 10/1996 | Lam |
| 5,591,197 A | 1/1997 | Orth et al. |
| 5,603,722 A | 2/1997 | Phan et al. |
| 5,605,696 A | 2/1997 | Eury et al. |
| 5,611,946 A | 3/1997 | Leong et al. |
| 5,656,186 A | 8/1997 | Mourou et al. |
| 5,720,894 A | 2/1998 | Neev et al. |
| 5,759,192 A | 6/1998 | Saunders et al. |
| 5,780,807 A * | 7/1998 | Saunders .................. 219/121.71 |
| 5,824,049 A | 10/1998 | Ragheb et al. |
| 5,854,805 A | 12/1998 | Reid et al. |
| 5,948,596 A | 9/1999 | Zhong et al. |
| 6,131,266 A | 10/2000 | Saunders et al. |
| 6,160,240 A | 12/2000 | Momma et al. |
| 6,208,458 B1 | 3/2001 | Galvanauskas et al. |
| 6,214,115 B1 | 4/2001 | Taylor et al. |
| 6,229,829 B1 | 5/2001 | Yin |
| 6,245,103 B1 | 6/2001 | Stinson |
| 6,248,129 B1 | 6/2001 | Froix |
| 6,254,632 B1 | 7/2001 | Wu et al. |
| 6,281,262 B1 | 8/2001 | Shikinami |
| 6,324,195 B1 | 11/2001 | Suzuki et al. |
| RE37,585 E | 3/2002 | Mourou et al. |
| 6,369,355 B1 | 4/2002 | Saunders |
| 6,395,326 B1 | 5/2002 | Castro et al. |
| 6,411,636 B1 | 6/2002 | Ota |
| 6,423,085 B1 | 7/2002 | Murayama et al. |
| 6,423,092 B2 | 7/2002 | Datta et al. |
| 6,489,589 B1 | 12/2002 | Alexander |
| 6,517,888 B1 | 2/2003 | Weber |
| 6,517,889 B1 | 2/2003 | Jayaraman |
| 6,521,865 B1 | 2/2003 | Jones et al. |
| 6,531,679 B2 | 3/2003 | Heerman et al. |
| 6,537,480 B1 | 3/2003 | Becker et al. |
| 6,558,733 B1 | 5/2003 | Hossainy et al. |
| 6,626,939 B1 | 9/2003 | Burnside et al. |
| 6,641,607 B1 | 11/2003 | Hossainy et al. |
| 6,653,426 B2 | 11/2003 | Alvarado et al. |
| 6,719,934 B2 | 4/2004 | Stinson |
| 6,878,901 B2 | 4/2005 | Johnson |
| 6,927,359 B2 | 8/2005 | Kleine et al. |
| 7,077,859 B2 | 7/2006 | Sirhan et al. |
| 2002/0082679 A1 | 6/2002 | Sirhan et al. |
| 2002/0082685 A1 | 6/2002 | Sirhan et al. |
| 2002/0198589 A1 | 12/2002 | Leong |
| 2003/0050692 A1 | 3/2003 | Sirhan et al. |
| 2003/0052101 A1 | 3/2003 | Gu et al. |
| 2003/0139801 A1 | 7/2003 | Sirhan et al. |
| 2004/0059408 A1 | 3/2004 | Alvarado et al. |
| 2004/0127970 A1 | 7/2004 | Saunders et al. |
| 2004/0226922 A1 | 11/2004 | Flanagan |
| 2004/0230290 A1 | 11/2004 | Weber et al. |
| 2005/0033412 A1 | 2/2005 | Wu et al. |
| 2005/0035101 A1 | 2/2005 | Jones et al. |
| 2005/0070996 A1 | 3/2005 | Dinh et al. |
| 2005/0087520 A1 | 4/2005 | Wang et al. |
| 2005/0159802 A1 * | 7/2005 | Furst et al. .................. 623/1.11 |
| 2005/0282407 A1 | 12/2005 | Bruland et al. |
| 2006/0033240 A1 | 2/2006 | Weber et al. |
| 2006/0041102 A1 | 2/2006 | Hossainy et al. |
| 2006/0054604 A1 | 3/2006 | Saunders |
| 2006/0232417 A1 * | 10/2006 | August et al. ............... 340/572.7 |
| 2007/0008534 A1 * | 1/2007 | Lo et al. ......................... 356/401 |
| 2008/0021307 A1 * | 1/2008 | Freeman et al. ............. 600/424 |
| 2008/0269870 A1 * | 10/2008 | Ruuttu et al. ................ 623/1.15 |

FOREIGN PATENT DOCUMENTS

| | | |
|---|---|---|
| EP | 0 372 789 A3 | 6/1990 |
| EP | 0 421 729 A2 | 4/1991 |
| EP | 0 540 290 A2 | 5/1993 |
| EP | 0 541 443 A1 | 5/1993 |
| EP | 0 562 150 A1 | 9/1993 |
| EP | 0 624 421 A2 | 11/1994 |
| EP | 0 662 307 A1 | 7/1995 |
| EP | 0 679 373 A2 | 11/1995 |
| EP | 0 714 641 A2 | 6/1996 |
| EP | 1466634 A1 | 10/2004 |
| GB | 2070490 A | 9/1981 |
| JP | 61169188 A | 7/1986 |
| JP | 5-285898 | 11/1993 |
| WO | 9206734 A1 | 4/1992 |
| WO | 2006009818 A2 | 1/2006 |
| WO | 2006056639 A1 | 6/2006 |

OTHER PUBLICATIONS

C.H. Fan et al., "Plasma Absorption of Femtosecond Laser Pulses in Dielectrics," Journal of Heat Transfer, Apr. 2002, vol. 124, pp. 275-283.

Brochure: Industrial Strength Laser Marking: Turning Photonix into Dollars, printed by Excel/Control Laser, Inc., 1992, Richard Stevenson.

Brochure: Anomatic TM II Positioning Controller, printed by Anorad Corporation (undated), 21 pages.

J. Sun et al., "Inert gas beam delivery for ultrafast laser micromachining at ambient pressure," Journal of Applied Physics, Jun. 13, 2001, vol. 89, No. 12, pp. 8219-8224.

* cited by examiner

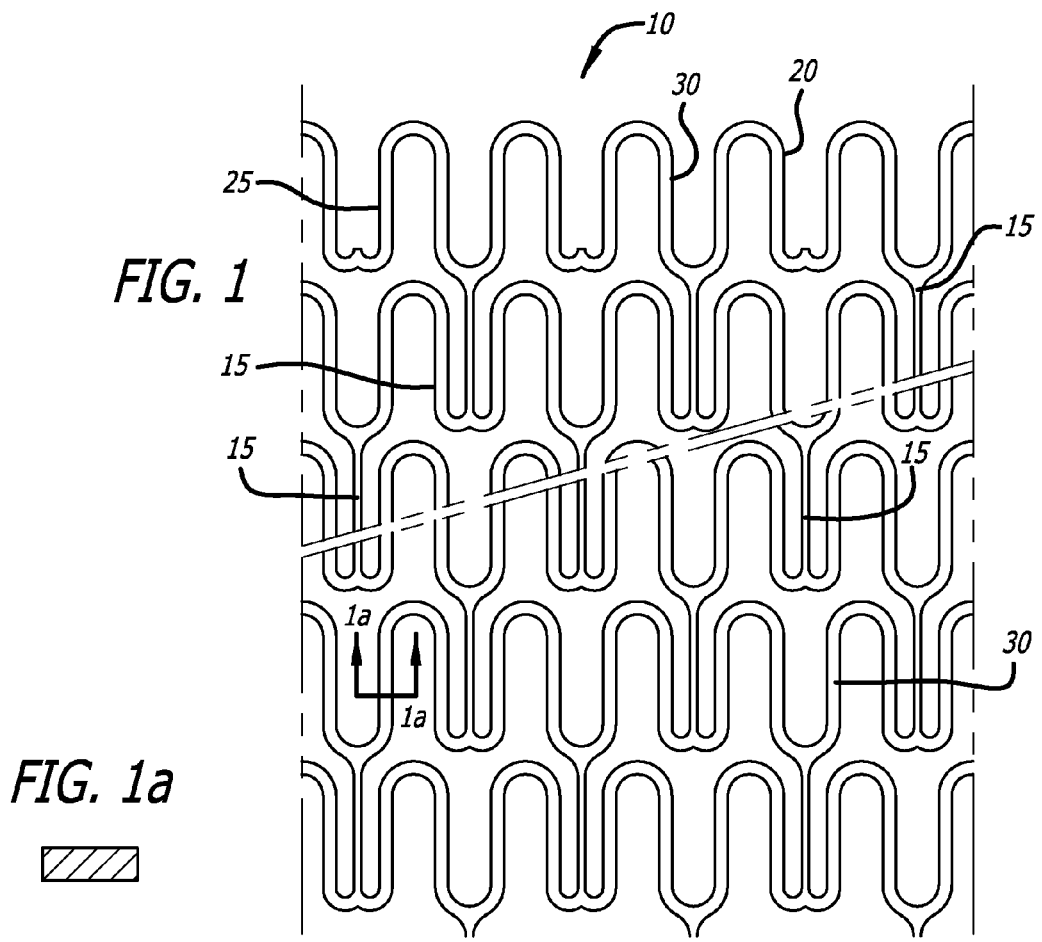
FIG. 1
FIG. 1a
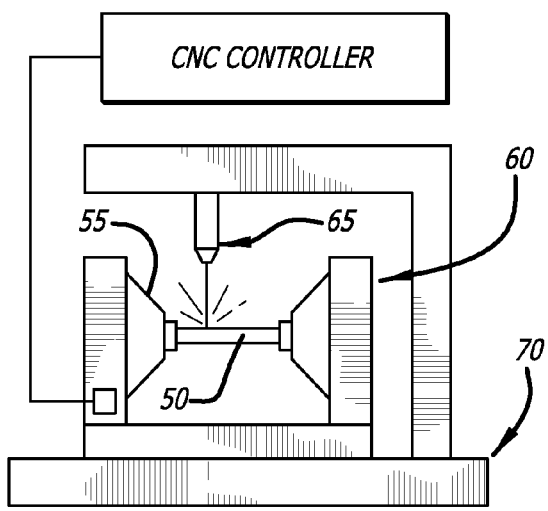
FIG. 2

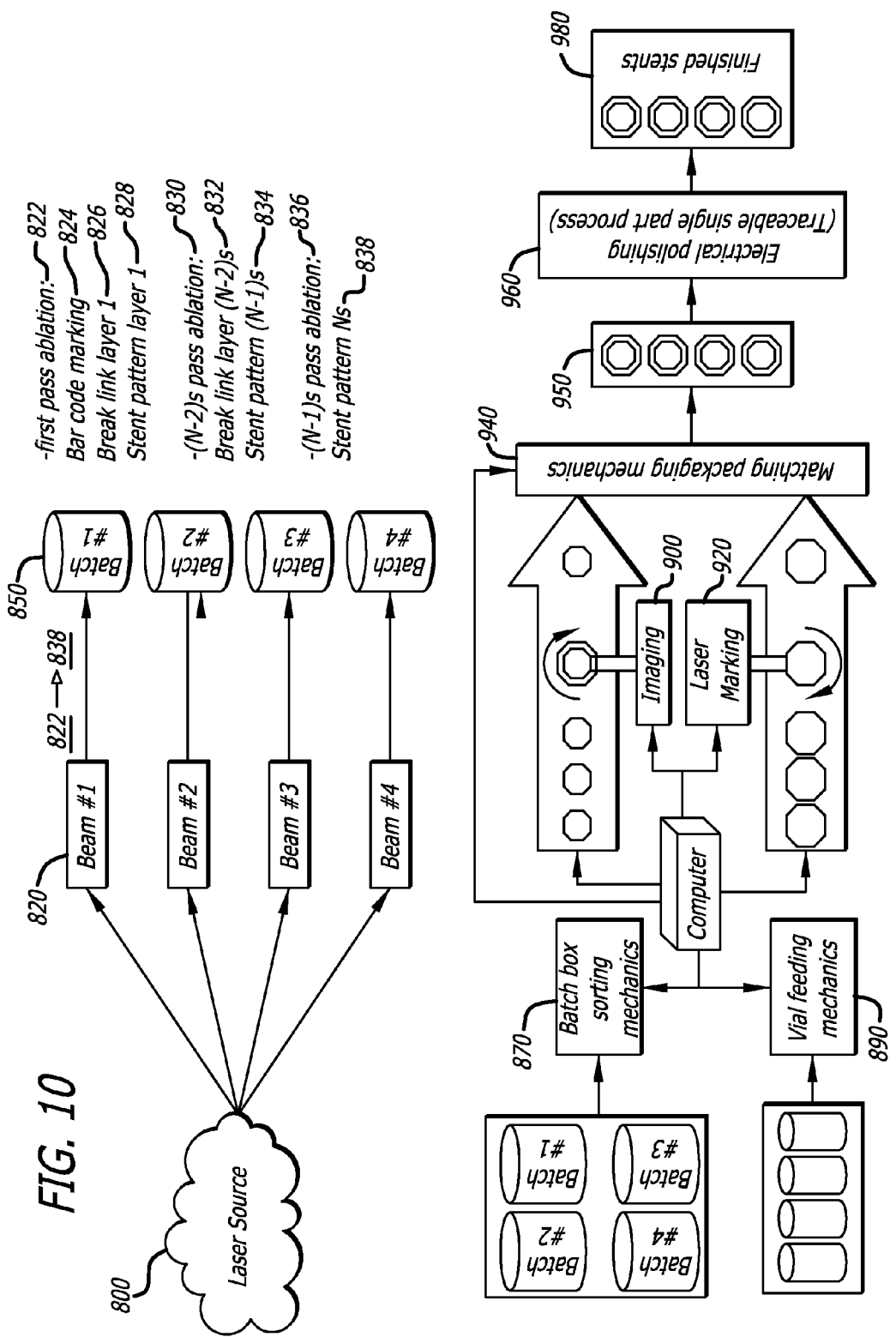

MULTIPLE BEAM LASER SYSTEM FOR FORMING STENTS

CROSS-REFERENCES TO RELATED APPLICATIONS

This application is a division of U.S. application Ser. No. 12/699,391, filed Feb. 3, 2010, now U.S. Pat. No. 8,461,478, issued Jun. 11, 2013, and claims priority from U.S. Provisional Application No. 61/149,621 filed Feb. 3, 2009 and U.S. Provisional Application No. 61/149,645 filed Feb. 3, 2009, incorporated by reference in their entireties.

This application is also related to U.S. application Ser. No. 12/699,262 entitled IMPROVED LASER CUTTING PROCESS FOR FORMING STENTS, filed Feb. 3, 2010, now U.S. Pat. No. 8,530,783, and U.S. application Ser. No. 12/699,335 entitled IMPROVED LASER CUTTING SYSTEM, filed Feb. 3, 2010.

BACKGROUND

1. Field of the Invention

The present invention relates generally to implantable medical devices and to a method for manufacturing implantable medical devices. These implantable medical devices may also be capable of retaining therapeutic materials and dispensing the therapeutic materials to a desired location of a patient's body. More particularly, the present invention relates to a method for forming the structure of a stent or intravascular or intraductal medical device.

2. General Background and State of the Art

In a typical percutaneous transluminal coronary angioplasty (PTCA) for compressing lesion plaque against the artery wall to dilate the artery lumen, a guiding catheter is percutaneously introduced into the cardiovascular system of a patient through the brachial or femoral arteries and advanced through the vasculature until the distal end is in the ostium. A dilatation catheter having a balloon on the distal end is introduced through the catheter. The catheter is first advanced into the patient's coronary vasculature until the dilatation balloon is properly positioned across the lesion.

Once in position across the lesion, a flexible, expandable, preformed balloon is inflated to a predetermined size at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty.

In angioplasty procedures of the kind referenced above, restenosis of the artery often develops which may require another angioplasty procedure, a surgical bypass operation, or some method of repairing or strengthening the area. To reduce the likelihood of the development of restenosis and strengthen the area, a physician can implant an intravascular prosthesis, typically called a stent, for maintaining vascular patency. In general, stents are small, cylindrical devices whose structure serves to create or maintain an unobstructed opening within a lumen. The stents are typically made of, for example, stainless steel, nitinol, or other materials and are delivered to the target site via a balloon catheter. Although the stents are effective in opening the stenotic lumen, the foreign material and structure of the stents themselves may exacerbate the occurrence of restenosis or thrombosis.

A variety of devices are known in the art for use as stents, including expandable tubular members, in a variety of patterns, that are able to be crimped onto a balloon catheter, and expanded after being positioned intraluminally on the balloon catheter, and that retain their expanded form. Typically, the stent is loaded and crimped onto the balloon portion of the catheter, and advanced to a location inside the artery at the lesion. The stent is then expanded to a larger diameter, by the balloon portion of the catheter, to implant the stent in the artery at the lesion. Typical stents and stent delivery systems are more fully disclosed in U.S. Pat. No. 5,514,154 (Lau et al.), U.S. Pat. No. 5,507,768 (Lau et al.), and U.S. Pat. No. 5,569,295 (Lam et al.).

Stents are commonly designed for long-term implantation within the body lumen. Some stents are designed for non-permanent implantation within the body lumen. By way of example, several stent devices and methods can be found in commonly assigned and common owned U.S. Pat. No. 5,002,560 (Machold et al.), U.S. Pat. No. 5,180,368 (Garrison), and U.S. Pat. No. 5,263,963 (Garrison et al.).

Intravascular or intraductal implantation of a stent generally involves advancing the stent on a balloon catheter or a similar device to the designated vessel/duct site, properly positioning the stent at the vessel/duct site, and deploying the stent by inflating the balloon which then expands the stent radially against the wall of the vessel/duct. Proper positioning of the stent requires precise placement of the stent at the vessel/duct site to be treated. Visualizing the position and expansion of the stent within a vessel/duct area is usually done using a fluoroscopic or x-ray imaging system.

Although PTCA and related procedures aid in alleviating intraluminal constrictions, such constrictions or blockages reoccur in many cases. The cause of these recurring obstructions, termed restenosis, is due to the body's immune system responding to the trauma of the surgical procedure. As a result, the PTCA procedure may need to be repeated to repair the damaged lumen.

In addition to providing physical support to passageways, stents are also used to carry therapeutic substances for local delivery of the substances to the damaged vasculature. For example, anticoagulants, antiplatelets, and cytostatic agents are substances commonly delivered from stents and are used to prevent thrombosis of the coronary lumen, to inhibit development of restenosis, and to reduce post-angioplasty proliferation of the vascular tissue, respectively. The therapeutic substances are typically either impregnated into the stent or carried in a polymer that coats the stent. The therapeutic substances are released from the stent or polymer once it has been implanted in the vessel.

In the past, stents have been manufactured in a variety of manners, including cutting a pattern into a tube that is then finished to form the stent. The pattern can be cut into the tube using various methods known in the art, including using a laser.

Laser cutting of the stent pattern initially utilized lasers such as the Nd:YAG laser, configured either at its fundamental mode and frequency, or where the frequency of the laser light was doubled, tripled, or even quadrupled to give a light beam having a desired characteristic to ensure faster and cleaner cuts.

Recently, lasers other than conventional Nd:YAG lasers have been used, such as diode-pumped solid-state lasers that operate in the short pulse pico-second and femto-second domains. These lasers provide improved cutting accuracy, but cut more slowly than conventional lasers such as the long pulse Nd:YAG laser. One approach to improving the efficiency of the pico-second and femto-second lasers has been to configure them so that the light from a single laser is split into multiple beams so that multiple stent with the same pattern, or different patterns, may be cut during a single cutting cycle. Such systems, however, must employ complex optical systems that, if not properly aligned, may reduce the cutting efficiency of the laser.

Present multiple beam laser systems typically include a quarter-wave plate through which a linear polarized laser beam is directed to produce a circular polarized beam. This circular polarized beam is then redirected through a high reflection mirror and a focusing lens to the work piece. The high-reflection mirror typically has high reflection for both s and p polarized beams. However, the phases for s and p polarized beams are not controlled. Therefore, after reflection, the s and p polarized beams will be reflected with different phase changes for each beam. Even with slightly different reflections, since the coating on the mirrors are not identical, resulting in slightly different reflectivity of the s and p beams, the circular polarized beam will become elliptically polarized because of the different phase changes. Such elliptically polarized laser beams have been found to be less efficient at cutting multi-directional patterns, such as are cut into stents.

This problem is further aggravated by polarization shifts induced when the laser beam travels through beam splitting mirrors. The polarization of one split beam may be significantly different from another split beam. As a result, tuning of the cutting laser beam is difficult because adjustment of one cutting laser beam polarization to an ideal state will necessarily adjust another laser beam to non-ideal state.

What has been needed, and heretofore unavailable, is an efficient and cost-effective multi-beam laser cutting system that is capable of being aligned so that the power level and spot size of each cutting beam can be individually controlled. Further, the system should also ensure that the light of each cutting beam delivered to the work piece is circularly polarized to optimize cutting quality and speed. Use of such a system will provide enhanced throughput, and may also include enhancements for tracking the manufacturing history of individual stents. The present invention satisfies these, and other needs.

SUMMARY OF THE INVENTION

The present invention is directed to an optical design for a multiple beam laser system. The various aspects of the present invention are an improvement over previously developed multiple beam laser systems because circular polarization is introduced to the laser beam after the beam reflects from the last mirror in the optical path. As a result, the cutting laser beam is maximally circular rather than elliptical or linear, which improves the cutting quality and efficiency for a multi-directional cutting pattern, such as is cut into a stent.

In another aspect, the invention also incorporates high-reflection mirrors and beam splitting mirrors with zero phase shifts in order to maintain the beam integrity and to ensure maximum circular polarization of the cutting laser beam.

In yet another aspect, the invention incorporates a quarter wave plate positioned downstream of all reflecting mirrors and beam splitting elements to maintain beam integrity and ensure maximum circular polarization of the laser beam.

In still another aspect, power level, polarization status and spot size of each of the independent lasers beams of the multiple beam laser system can be controlled, resulting in improvements in the efficiency and economy which allows for scaled up manufacturing of precision-machined parts, such as stents. Moreover, tuning of each laser beam to provide a maximally circularized polarized light beam at the work part ensures an efficient and high-quality laser cut.

In a further aspect, the inventions comprises a multiple beam laser system, including a laser capable of emitting a linearly polarized laser beam, at least one partially transmissive and partially reflective mirror capable of transmitting and reflecting the linearly polarized laser beam, the partially transmissive and partially reflective mirror being used to divide a single laser beam into two laser beams, a half wave plate, the half wave plate being capable of being rotated to alter the polarization direction of the incoming laser beam, a polarizer, which, along with the half wave plate provides an attenuation feature for adjusting the power level of the laser beam, an adjustable beam expander for adjusting the spot size and also for compensating for other optical defects caused by variation of the raw laser beam size or in the performance of other optical elements in the optical path, a quarter-wave plate positioned after all other mirrors and beam splitters in the optical path, and for introducing circular polarization into the laser beam and a focal lens for focusing the laser beam on a work piece.

In a further aspect, the invention provides a method of manufacturing stents using an automated process that allows for batching of stents as required. The automation process includes packaging, identification, and marking systems that permit material control and lot history to be maintained for effective traceability. Finished stents produced by this process can be delivered as input material for manufacturing a stent delivery system. Since the process is automated and permits some degree of action, it is possible to run the process at full capacity continuously, thereby fully utilizing the laser systems and minimizing costs associated with laser downtime.

In another aspect, the system and method of the present invention provides an automated system for manufacturing stents utilizing, among other processes and equipment, multiple laser beams formed from a single laser source.

In yet another aspect, the present invention includes using a laser to cut an identification tag from a tube as part of a stent pattern being cut to form a stent. The tag includes information related to the manufacturing history of the stent.

In still another aspect, the present invention includes a multiple beam laser system, comprising: a laser capable of emitting a linearly polarized laser beam; at least one partially transmissive and partially reflective beam splitter capable of transmitting and reflecting the laser beam at a nearly linear polarization and which introduces no polarization change to the laser beam and which is capable of dividing the laser beam emitted by the laser into two laser beams; a half wave plate disposed in an optical path of a selected one of the laser beams, the half wave plate being capable of being rotated to alter the polarization direction the laser beam; a polarizer disposed in the optical path of the selected laser beam for adjusting the laser power of the selected laser beam at a selected polarization direction; an adjustable beam expander disposed in the optical path of the selected laser beam to adjust the size of the selected laser beam; a quarter-wave plate disposed in the selected beam after the beam splitter for introducing circular polarization into the selected laser beam; and a focusing lens for focusing the selected laser beam to a desired spot size.

In another aspect, the beam expander is disposed in the optical path downstream of the polarizer. In yet another aspect, the beam expander is disposed in the optical path upstream of the polarizer. In still another aspect, the half wave plate is disposed upstream of the polarizer. In still another aspect, the quarter wave plate is disposed downstream of the polarizer.

In an even further aspect, a second polarizer is disposed in the optical path of a second selected one of the laser beams; and a second beam expander is disposed in the optical path of the second selected one of the laser beams upstream from the second polarizer. In another aspect, the polarizer is disposed in the between the laser and the at least one partially transmissive and partially reflective mirror.

In still another aspect, a power meter is disposed in the optical path of the laser beam to measure the power of the laser beam.

In yet another aspect, the invention includes an achromatic lens; a camera configured to view the cutting process through the achromatic lens; and a dichroic mirror for reflecting the selected laser beam and for providing an optical pathway allowing the camera to view the cutting process. In another aspect, the dichroic mirror is a long wave pass mirror.

In a further aspect, the invention also includes a system for identifying a stent, comprising: a laser for providing a laser beam; a computer controlled locating fixture for moving a tube in a selected manner beneath the laser beam to cut a pattern into the tube, the pattern representing information related to the identification of a stent to be cut from the tube.

In another aspect, the pattern includes a tag upon which information is etched by the laser beam, and in still another aspect, the pattern is a bar code.

In a still further aspect, the invention includes a method for manufacturing stents using a multiple beam cutting process comprising: splitting a laser beam into at least two laser beams; cutting a stent pattern into a tube using one of the at least two laser beams; marking the stent pattern with an identifier; sorting a batch of stents into individual stents; reading the identifier on an individual stent; marking information related to the identifier on a vial; and placing the individual stent into the marked vial.

In a further aspect, the invention also includes removing remove the identifier from the stent. In still another aspect, removing the identifier includes electrochemically polishing the stent to remove the identifier, and in still another aspect, removing the identifier includes cutting the identifier from the stent.

In yet another aspect, reading the identifier on the stent includes: digitizing the identifier; and storing the digitized identifier in a memory in operable communication with a processor. In still another aspect, marking information related to the identifier on a vial includes: reading the digitized identifier of a stent from the memory; associating the digitized identifier with data related to the manufacture of the stent; marking selected data related to the manufacture of the stent on the vial.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a partial view of a stent showing various elements of the stent pattern.

FIG. 1A is a cross-sectional view of a portion of one of the elements of the stent pattern.

FIG. 2 is a side view of a typical arrangement of a computer controlled cutting system using a laser beam to cut stent patterns into tubing to form a stent.

FIG. 10 is a schematic layout of one embodiment of an automated stent manufacturing process utilizing multiple cutting beams from a single laser source.

DETAILED DESCRIPTION OF THE PREFERRED EMBODIMENTS

Figure 3:
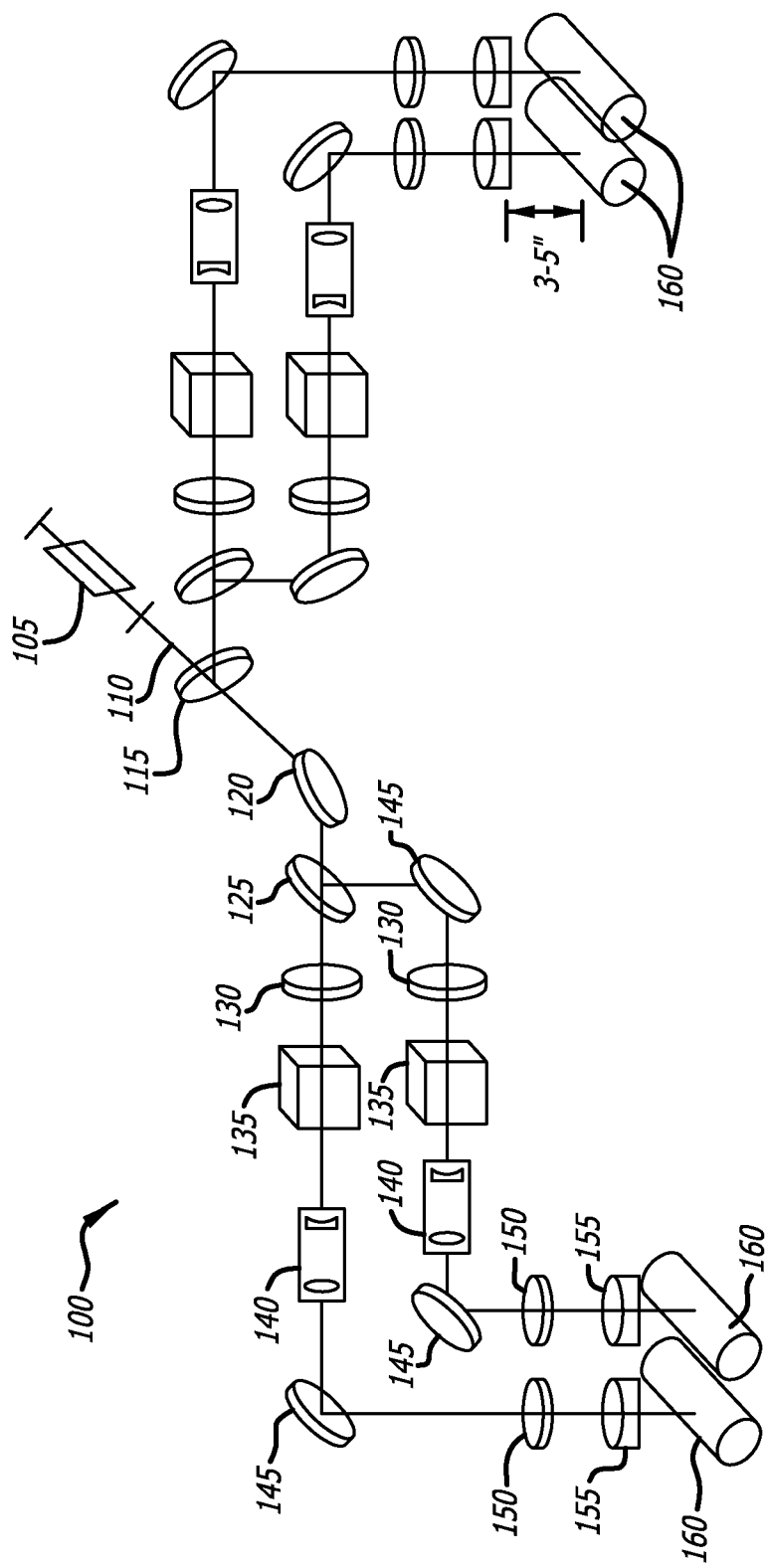
FIG. 3 is a schematic design of an embodiment of an optical layout for a multiple beam laser system in accordance with principles of the present invention.

FIG. 1 is an enlarged perspective view of a stent 10 illustrating an exemplary stent pattern and showing the placement of interconnecting elements 15 between adjacent radially expandable cylindrical elements. Each pair of the interconnecting elements 15 on one side of a cylindrical element are preferably placed to achieve maximum flexibility for a stent. In the embodiment shown in FIG. 1, the stent 10 has three interconnecting elements 15 between adjacent radially expandable cylindrical elements which are 120 degrees apart. Each pair of interconnecting elements 15 on one side of a cylindrical element are offset radially 60 degrees from the pair on the other side of the cylindrical element. The alternation of the interconnecting elements results in a stent which is longitudinally flexible in essentially all directions. Various configurations for the placement of interconnecting elements are possible. However, as previously mentioned, all of the interconnecting elements of an individual stent should be secured to either the peaks or valleys of the undulating structural elements in order to prevent shortening of the stent during the expansion thereof.

The number of undulations may also be varied to accommodate placement of interconnecting elements 15, for example, at the peaks of the undulations or along the sides of the undulations as shown in FIG. 1.

As best observed in FIG. 1, cylindrical elements in this exemplary embodiment are shown in the form of a serpentine pattern. As previously mentioned, each cylindrical element is connected by interconnecting elements 15. The serpentine pattern is made up of a plurality of U-shaped members 20, W-shaped members 25, and Y-shaped members 30, each having a different radius so that expansion forces are more evenly distributed over the various members.

The afore-described illustrative stent 10 and similar stent structures can be made in many ways. However, the preferred method of making the stent is to cut a thin-walled tubular member, such as, for example, stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser, as exemplified schematically in FIG. 2.

The tubing may be made of suitable biocompatible material such as, for example, stainless steel. The stainless steel tube may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants. Other biomaterials may also be used, such as various biocompatible polymers, co-polymers or suitable metals, alloys or composites that are capable of being cut by a laser.

Another example of materials that can be used for forming stents is disclosed within U.S. application Ser. No. 12/070,646, the subject matter of which is intended to be incorporated herein in its entirety, which application discloses a high strength, low modulus metal alloy comprising the following elements: (a) between about 0.1 and 70 weight percent Niobium, (b) between about 0.1 and 30 weight percent in total of at least one element selected from the group consisting of Tungsten, Zirconium and Molybdenum, (c) up to 5 weight percent in total of at least one element selected from the group consisting of Hafnium, Rhenium and Lanthanides, in particular Cerium, (d) and a balance of Tantalum The alloy provides for a uniform beta structure, which is uniform and corrosion resistant, and has the ability for conversion oxidation or nitridization surface hardening of a medical implant or device formed from the alloy. The tungsten content of such an alloy is preferably between 0.1 and 15 weight percent, the zirconium content is preferably between 0.1 and 10 weight percent, The molybdenum content is preferably between 0.1 and 20 weight percent and the niobium content is preferably between 5 and 25 weight percent.

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch or less.

Referring now to FIG. 2, the tubing 50 is put in a rotatable collet fixture 55 of a machine-controlled apparatus 60 for positioning the tubing 50 relative to a laser 65. According to machine-encoded instructions, the tubing 50 is rotated and moved longitudinally relative to the laser 65 which is also machine-controlled. The laser selectively removes the material from the tubing and a pattern is cut into the tube. The tube is therefore cut into the discrete pattern of the finished stent.

The process of cutting a pattern for the stent into the tubing is automated except for loading and unloading the length of tubing. Referring again to FIG. 2, it may be done, for example, using a CNC-opposing collet fixture 55 for axial rotation of the length of tubing, in conjunction with a CNC X/Y table 70 to move the length of tubing axially relatively to a machine-controlled laser as described. Alternatively, the collet fixture may hold the tubing at only one end, leaving the opposite end of the tubing unsupported. The entire space between collets can be patterned using the laser. The program for control of the apparatus is dependent on the particular configuration used and the pattern to be cut by the laser.

Referring now to FIG. 3, there is illustrated an exemplary embodiment of a multiple beam laser system incorporating various aspects of the present invention. The advantage of using a multiple beam laser system is that it splits the beam of a single laser source and directs the split beams toward individual working parts to cut stent patterns into the working parts. Using such a system results in improved throughput because multiple laser beams allow multiple stent patterns to be cut in the same time as a single stent pattern may be cut using a single laser beam apparatus, thus maximizing the use of an expensive laser having a relatively slow cutting speed, such as a pico-second or femto-second laser.

In prior art systems, a linearly polarized laser beam is directed through a quarter-wave plate to produce a circular polarized beam. This circular polarized beam is then redirected through a high reflection mirror and a focusing lens to the work piece. The normal high reflection mirror has high reflection for the both the s and p beam components. However, in prior art systems, the phases of the s and p beams are not controlled. Thus, the circularly polarized beam becomes elliptically polarized because of the phase changes. In addition, the coating on various optical elements in the system may be imperfect, resulting in slightly different reflectivity for the s and p beam components. Laser beams with elliptical polarization have been found to be less efficient at cutting multi-directional stent patters, and are undesirable.

This problem of polarization change is aggravated by the beam splitting mirrors in the multiple beam system because the polarization of one split beam may be significantly different from another split beam. As a result, tuning of the cutting laser beam is difficult because adjustment of one cutting laser beam polarization to an ideal state will necessarily adjust another beam to a non-ideal state.

FIG. 3 shows a multiple laser beam system 100 having a laser source 105. Laser source 105 may be a short-pulse, high-intensity laser such as a pico-second laser. Those skilled in the art will appreciate that other laser sources may be used without departing from the scope of the invention, including, but not limited to, gas laser such as carbon dioxide, carbon monoxide, solid-state lasers such as Nd:YAG, ytterbium or any other laser capable of producing a beam that can cut a stent pattern.

Laser 105 produces an s polarized laser beam 110 that is directed at a beam splitter 115 that is partially transmissive and partially reflective, which transmits and reflects the beam at linear polarization. The transmitted beam and the reflected beam remain in linear polarization even if the beam splitter 115 has slightly different reflectivity/transmissivity and a different phase shift.

The linearly polarized laser beam may then be split by partial transmitting/reflecting beam splitter 125, resulting in multiple potential cutting beams. Once again, in this arrangement, the beam splitter 125 does not change the linear polarization of the beam even if the beam splitter has slightly different reflectivity/transmissivity and a different phase shift. These beams may be directed to additional partial transmitting/reflecting mirrors as necessary either immediately or after modification by other optical components, to split the beams into further cutting beams.

Once an independent cutting laser beam is formed in this manner, it will interact with a number of optical components to produce an idealized cutting laser beam with desired power, spot size, and polarization characteristics. As will be discussed in more detail below, these characteristics can be individually controlled.

The power of the laser beam is controlled using a combination of a half wavelength plate 130 and a polarizer 135. Half wave plate 130 can be rotated as needed to change the polarization direction of the incoming linearly polarized laser beam. As the modified laser beam exits the half wave plate 130 and travels through the polarizer 135, polarizer 135 filter the light based on the match between the incoming laser polarization and the polarizer construction. By rotating the half-wave plate 130, the laser beam output of the polarizer can vary between a maximum when the incoming light polarization matches ideally with the polarizer orientation and a minimum when the incoming light polarization is perpendicular to the polarizer orientation. The output of polarizer 135 determines the power of the cutting laser beam. The half wave plate 130 and polarizer 135 also maintain the linear polarization of the laser beam as it travels towards the working part, which is important to allow for optimal circular polarization of the laser beam at the cutting surface.

At any point after laser beam 110 exits polarizer 135, it may be passed through an adjustable beam expander 140 that is capable of modifying the spot size of the laser beam without modifying the polarization of the laser beam. It will be appreciated that various layout of the optical components of the laser system depicted in FIG. 3 are possible, such as positioning the adjustable beam expander 140 closer to the working part. Due to space requirements of the adjustable beam expander 140, however, a more compact system may be achieved, if necessary, by positioning the adjustable beam expander as shown in FIG. 3. One example of an adjustable beam expander that is suitable for use in the described system is the model EPZ-13C-THG for 355 nm laser light made by BeamExpander.com LLC.

The laser beam may be reflected by one or more highly reflective mirrors 145. In a preferred embodiment, these mirrors have a high reflectivity for the laser beam, that is, greater than 99%. Minors 145 also maintain the linear polarization of the laser beam 110 as it travels toward the working part 160. In another embodiment, mirror 145 may be replaced by an optical element having a coating which allows for a high reflection for the laser cutting beam, and high transmission for the an illumination light to provide for lighting of the work piece so it can be view by an on-line camera or other viewing device.

Prior to reaching working part 160, but after reflecting from the last mirror 145 in the optical path, the laser beam 110 passes through a quarter wave plate 150 that introduces circular polarization into the laser beam 110. Maintenance of linearity polarization in the laser beam until it passes through quarter wave plate 150 is important in that elliptical polarization of the laser beam may result otherwise. Circular polarization of the laser beam 110 when it impinges on the material to be cut results in a more efficient and higher quality cut of the working part.

Depending on the overall design requirements of the laser cutting stations, the beam may pass through lenses 155 or other polarization insensitive optical components after the beam has passed through the quarter wave plate 150 as long as the polarization of the laser beam is not modified.

While the components of only two of the beam arms have been identified with reference numerals in FIG. 3, it will be appreciated that the additional two beam arms of FIG. 3 may be identical to the numbered beam arms. Alternatively, the additional beam arms may include more or less optical components as required by the design needs of the cutting stations, so long as the polarization of the resultant laser beam at the work surface is ideally circularly polarized.

It will be appreciated by those skilled in the art that the optical design of the laser cutting system depicted in FIG. 3 produces multiple laser beams, with each laser beam being individually controllable with respect to power level, polarization status, and spot-sized characteristics. For example, polarization of the laser beam is controlled by polarizer 135 and quarter wave plate 150 and power level is controlled by polarizer 135 and half wave plate 130. Spot size is controlled using a combination of adjustable beam expander 140 and focusing lenses 155. In an alternative embodiment, an extra modulator and switch may be used to control the repetition rate, power level and on/off control of each individual laser beam.

Figure 4:
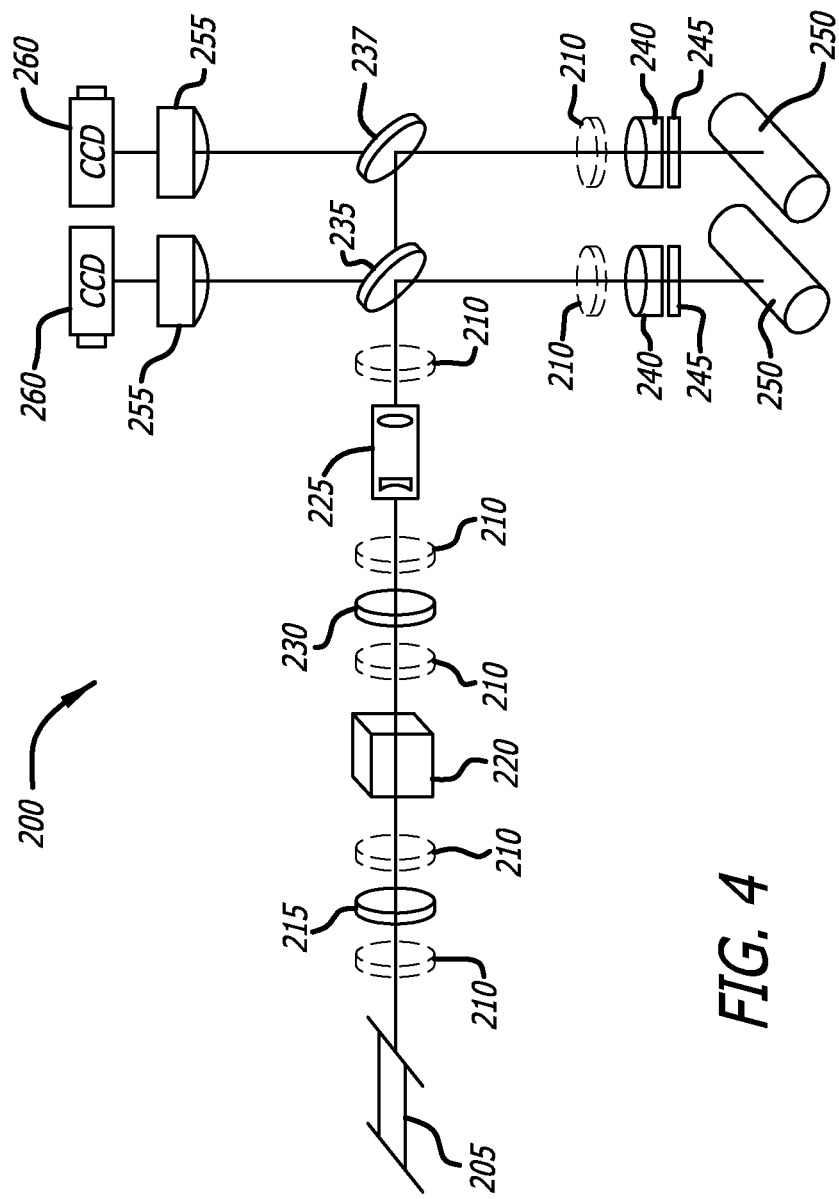
FIG. 4 is a schematic design of an embodiment of an optical layout for a multiple beam laser system which typically produces elliptically polarized beams which cannot be individually controlled.

FIG. 4 is a schematic of an optical layout which is capable of producing circularly polarized beams. In this layout, however, the two beams cannot be individually controlled. In this embodiment, laser light is produced by a linearly p[polarized laser 205 which is directed through a half wave plate 215, through a polarizer 220, then through a quarter wave plate 230 to generate a circularly polarized beam. The circularly polarized laser beam then passes through an adjustable beam expander 225, which is used to control the ultimate spot size of the beam. The circularly polarized beam impinges upon partial beam splitter 235, where a portion of the beam is reflected downwards through a focusing lens 240 to cut a stent pattern into a work piece 250. A portion of the laser beam is also transmitted through beam splitter 235 to a long wave pass dichroic mirror 237, where the laser beam is reflected downwards through a focusing lens 240 to cut a stent pattern into a second work piece 250. A protection window 245 may be disposed between the focusing lens 240 and the work piece 250 to prevent contamination of the optical system from debris generated during the cutting process.

Returning again to beam splitter 235, an illumination light and a view of the laser beam falling upon the work piece may also be transmitted upwards through an achromatic lens 255 to fall upon a charge couple device 260. This assembly allows for beam alignment on the work piece and monitoring cutting status. Similarly, an illumination light and a view of the cutting beam on the work piece may be transmitted upwards through an achromatic lens 255 to fall upon a second charge couple device 260. It should be noted that because the polarizer 220 and beam expander 225 are located prior to the beam-splitting mirror 235, the beams cannot be individually controlled, which may result in the two laser beams having different power levels and spot sizes. This may also be disadvantageous if any elliptical polarization is introduced to laser beam by mirror 235 or mirror 237, which can occur since the once circularly polarized beam passes through the beam splitter 235 and mirror 237 which may introduce different reflectivity/transmissivity and phase shift to the s and p beam components.

Figure 5:
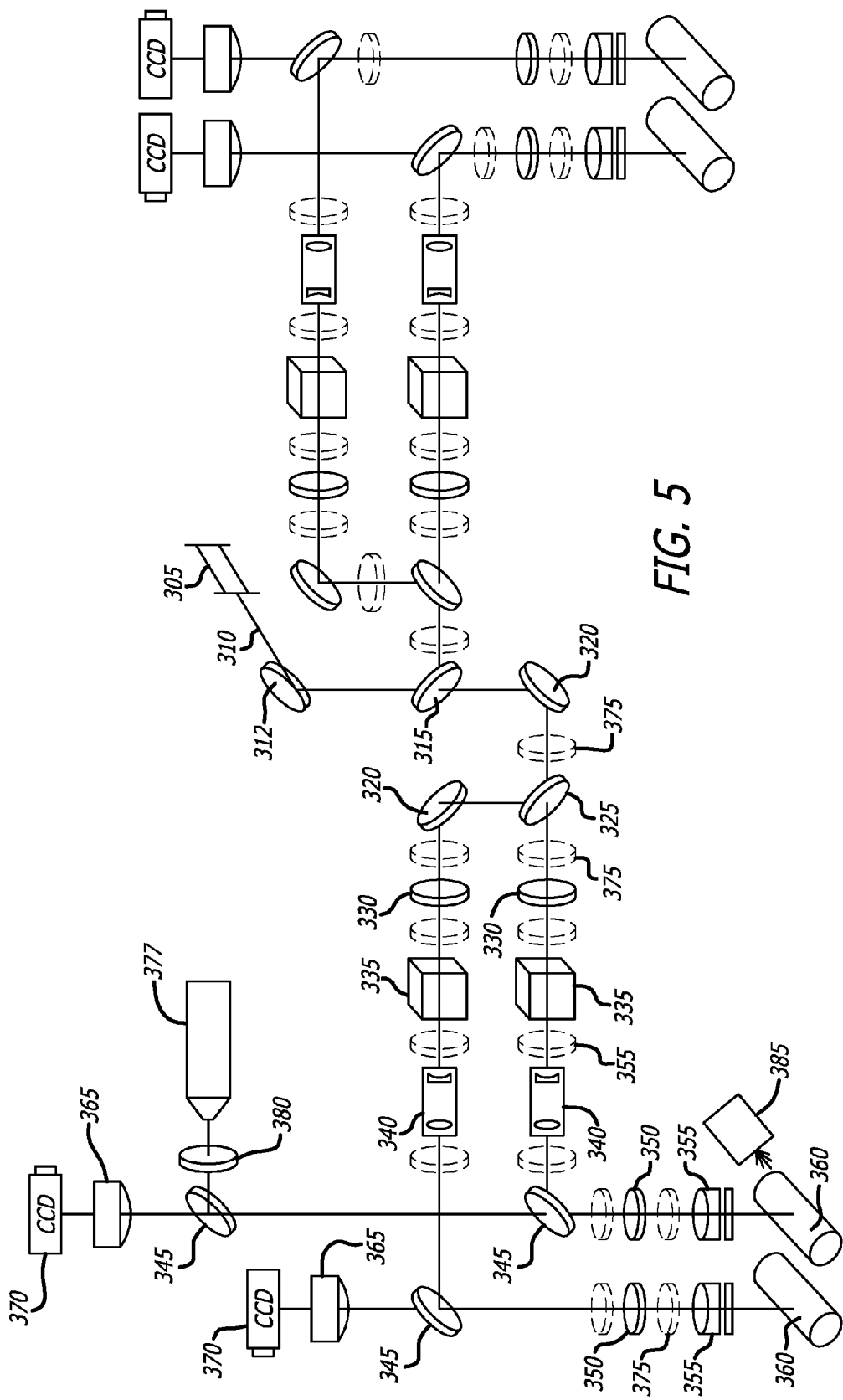
FIG. 5 is a schematic design of yet another embodiment of an optical layout for a multiple beam laser system in accordance with the principles of the present invention. An online vision system having on-axis or off-axis illumination is also illustrated.

FIG. 5 depicts another embodiment of an optical layout similar to the optical layout set forth with regard to FIG. 3. In FIG. 5 charge couple devices and achromatic lenses have been added to allow for monitoring of the individual laser cutting status.

In the embodiment illustrated in FIG. 5, a laser 305 produces a linearly polarized laser beam 310 that is directed at a mirror high reflection mirror 312 maintains the linear polarization of the laser beam. Linearly polarized laser beam 310 is then directed at beam splitter 315 that is partially transmissive and partially reflective, which transmits and reflects the beam at linear polarization. The transmitted beam and the reflected beam remain in linear polarization even if the beam splitter has slightly different reflectivity/transmissivity and a different phase shift.

The transmitted portion of laser beam 310 in this embodiment may then be redirected by reflective mirror 320, which also keeps the reflected beam linearly polarized. The portion of the laser beam reflected by mirror 315 may, as illustrated, provide a laser source for at least one other laser optical train that may be used to cut yet another work piece.

After being reflected by mirror 320, the laser beam 310 may then be split by partial transmitting/reflecting mirror 325, resulting in two cutting beams. These beams may be directed to additional partial transmitting/reflecting mirrors as necessary either immediately or after modification by other optical components, to split the beams into further cutting beams.

Once an independent cutting laser beam is formed in the manner described above, it will interact with a number of optical components to produce an idealized cutting laser beam with desired power, spot size, and polarization characteristics which can be individually controlled Similar to the laser system described above with reference to FIG. 3, the power of each individual laser beam is controlled using a combination of a half wavelength plate 330 and a polarizer 335. Half wave plate 330 can be rotated as needed to change the polarization direction of the incoming laser beam. As the modified laser beam exits the half wave plate 330 and travels through the polarizer 335, polarizer 335 filters the light based on the match between the incoming laser polarization and the polarizer construction. By rotating the half-wave plate 330, the laser beam output of the polarizer can vary between a maximum when the incoming light polarization matches ideally with the polarizer orientation, and a minimum when the incoming light polarization is perpendicular to the polarizer orientation. The output of polarizer 335 determines the power of the cutting laser beam. The half wave plate 330 and polarizer 335 also maintain the linear polarization of the laser beam as it travels towards the working part, which is important to allow for optimal circular polarization of the laser beam at the cutting surface.

At any point after laser beam 310 exits polarizer 335, it may be passed through an adjustable beam expander 340 that is capable of modifying the spot size of the laser beam without modifying the polarization of the laser beam.

The laser beam may be reflected by one or more highly reflective mirrors 345. In a preferred embodiment, these mirrors have a high reflectivity and include a coating that provides no power reduction of the laser beam as it is reflected and transmit the illuminated light so that the focused cutting spot of the laser beam cutting the work piece can be imaged onto the charge coupled device. Minors 345 also maintain the linear polarization of the laser beam 310 as it travels toward the work piece 360.

Prior to reaching work piece 360, but after reflecting from the last mirror 345 in the optical path, the linearly polarized laser beam 310 passes through a quarter wave plate 350 that introduces circular polarization into the laser beam 310.

Depending on the overall design requirements of the laser cutting stations, the beam may pass through lenses 355 or other polarization insensitive optical components after the beam has passed through the quarter wave plate 350 as long as the polarization of the laser beam is not modified.

While the components of only two of the beam arms have been identified with reference numerals in FIG. 5, it will be appreciated that the additional two beam arms of FIG. 3 may be identical to the numbered beam arms. Alternatively, the additional beam arms may include more or less optical components as required by the design needs of the cutting stations, so long as the polarization of the resultant laser beam at the work surface is ideally circularly polarized.

Another feature of the system depicted in FIG. 5 is the use of a charge-coupled device 370 and achromatic lens 365 assembly for monitoring laser cutting. Additionally, power meters 375 may be inserted along the optical path in selected locations to monitor the power of laser beam 310.

In yet another embodiment, the system may include a mirror 345 in the optical paths of one, two or more of the individual beams arranged so that an off-axis light 377 can be used to illuminate the work piece 360 so that the cutting status of the stent can be monitored using charge couple device 370. A focusing lens 380 may also be used to focus the illumination light as required. In another embodiment, an off-axis light 385 may be used to illuminate the work piece 360.

Figure 6:
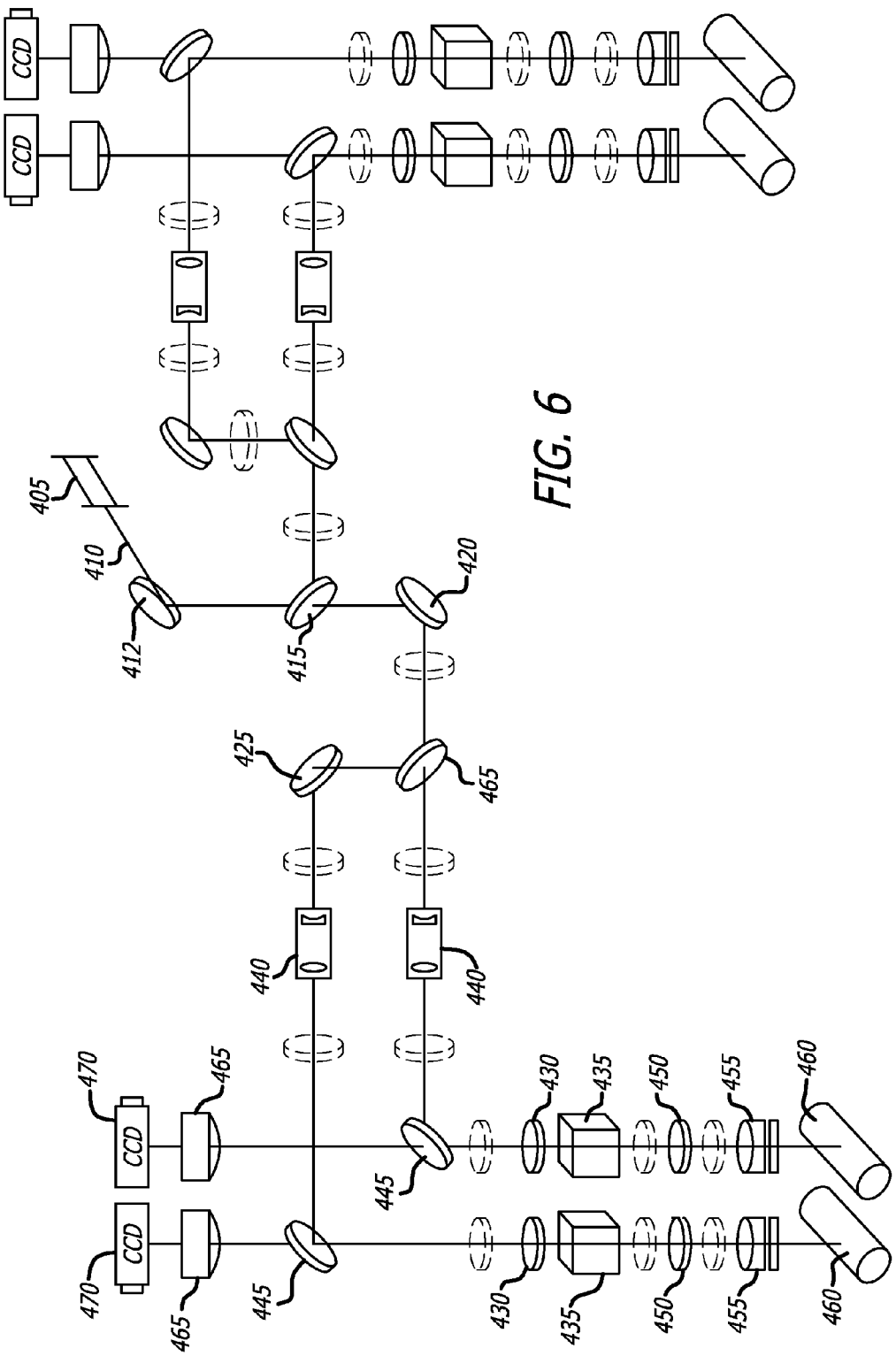
FIG. 6 is an alternative embodiment of the optical layout of FIG. 5 showing placement of the wave plates and polarizer downstream of the beam expander.

FIG. 6 illustrates an alternative embodiment of the system shown in FIG. 5 with the exception that the wave plates 430 and polarizer 435 are located in the laser beam at a point after the beam has passed through the beam expander 440.

In this embodiment, the initial portion of the optical path including laser 405, reflecting mirror 412, reflecting/transmitting mirror 415, reflecting mirror 420 and reflecting mirror 425 and reflecting mirror 420 are similar to that described with reference to FIG. 5. The embodiment of FIG. 6 diverges from the embodiment of FIG. 5 after the two cutting beams are formed. In this embodiment, laser beam 410 passes through beam expander 440 and then is reflected by mirror 445 to pass through half wave plate 430 and polarizer 450 on its way to work piece 460. Note that this arrangement still allows for control of the power, polarization and spot size of each individual cutting beam.

Figure 7:
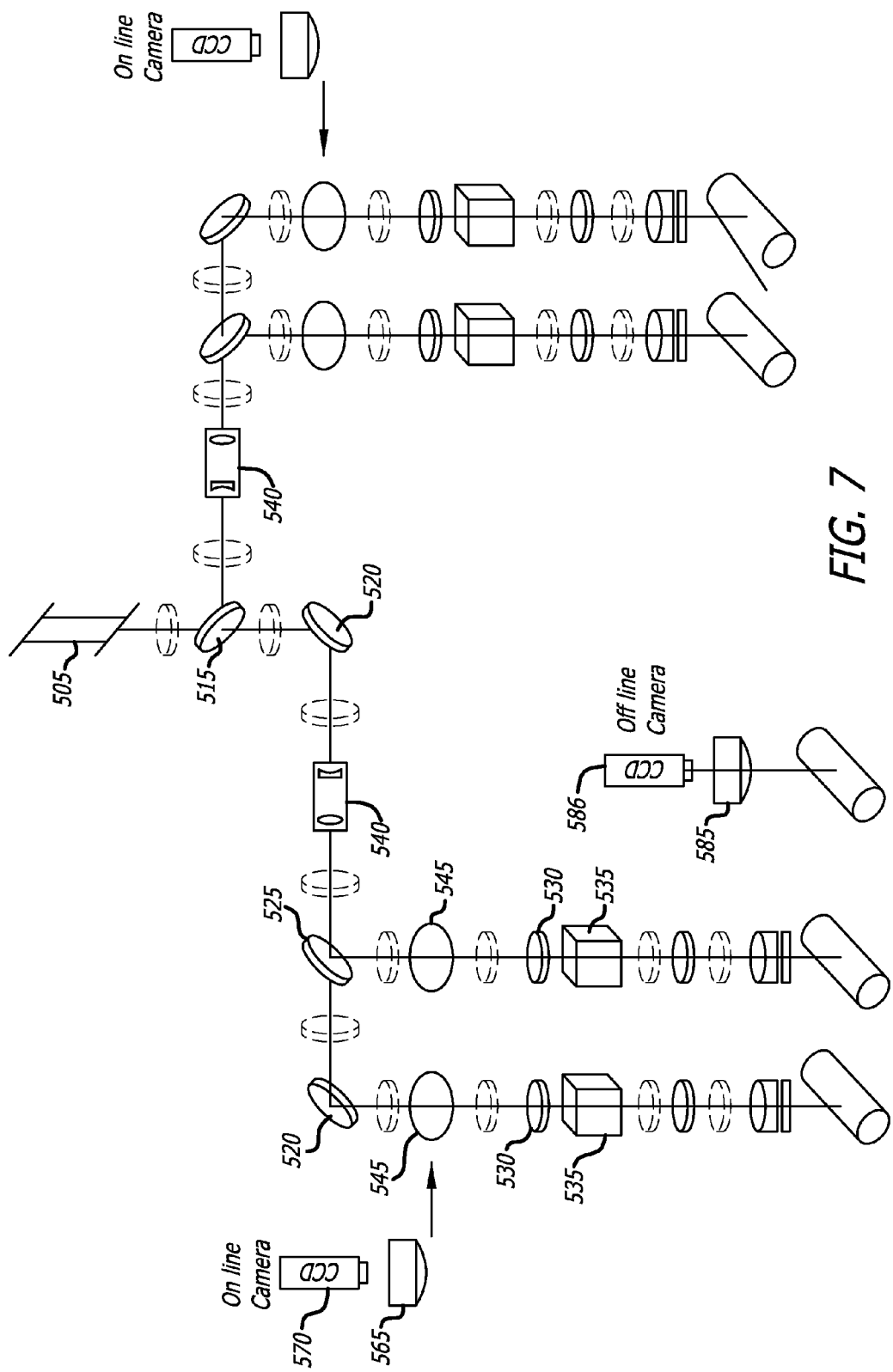
FIG. 7 is another alternative embodiment of the optical layout of FIG. 5 showing the beam expander placed in the optical path after the laser beam has been split once.

FIG. 7 depicts another embodiment of an optical layout wherein the light from the laser source 505 is split into two beams. Each laser beam then passes through a beam expander 540. The split laser beam is then split again in each arm to form four laser beams which are then directed through half wave plates 530 and polarizers 535 before being focused onto a work piece. The embodiment of FIG. 7 also shows placement of online CCD cameras 570 and achromatic lenses 565, as well as an offline camera 580, which may be a charge couple device, and achromatic 585 lens for viewing the cutting process. The advantage of this embodiment is that it allows for the use of only two beam expanders, rather than the four beam expanders required in other embodiments. One disadvantage, however, is that spot size uniformity will not be maintained at the same levels as the embodiments shown in FIG. 3, 5 or 6 because the spot size of each laser beam is not individually adjustable.

Figure 8:
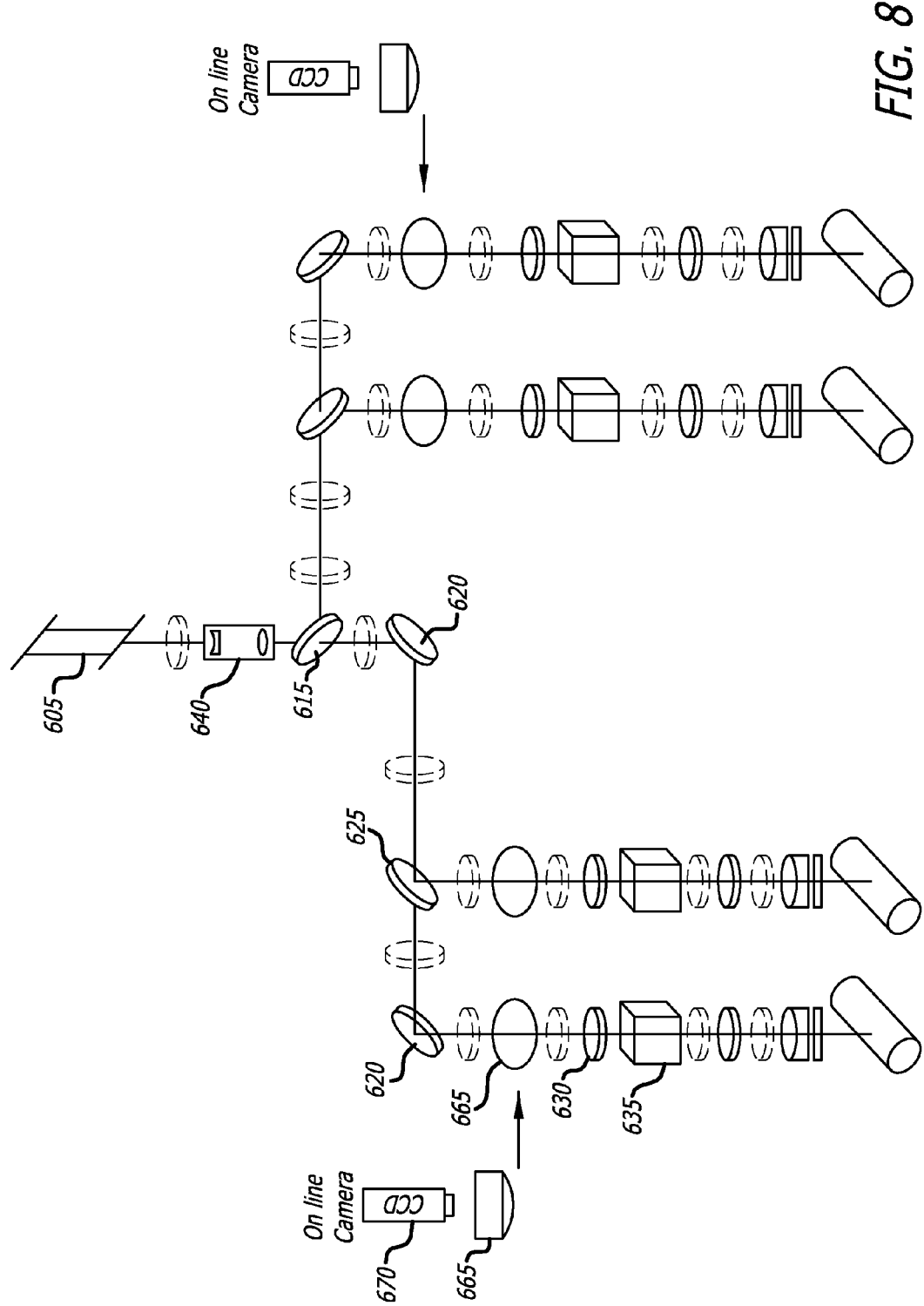
FIG. 8 is a schematic design of an alternative embodiment of the optical layout of FIG. 6 wherein a beam expander is inserted into the optical path before the light beam from the laser has been split.

FIG. 8 is another embodiment of an optical layout wherein a beam expander is inserted into the optical path before the laser beam from the laser source 605 is split. The advantage of this embodiment is that it requires only a single beam splitter 640. Of course, the disadvantage is that spot size uniformity will not be maintained at the same levels as other embodiments because the spot size of each laser beam will not be individually adjustable. Note, however, that because each beam passes through half wave plate 630 and polarizer 635, the polarization of each beam is individually adjustable, ensuring that the beam spot is circularly polarized when it shines upon the work piece.

Figure 9A:
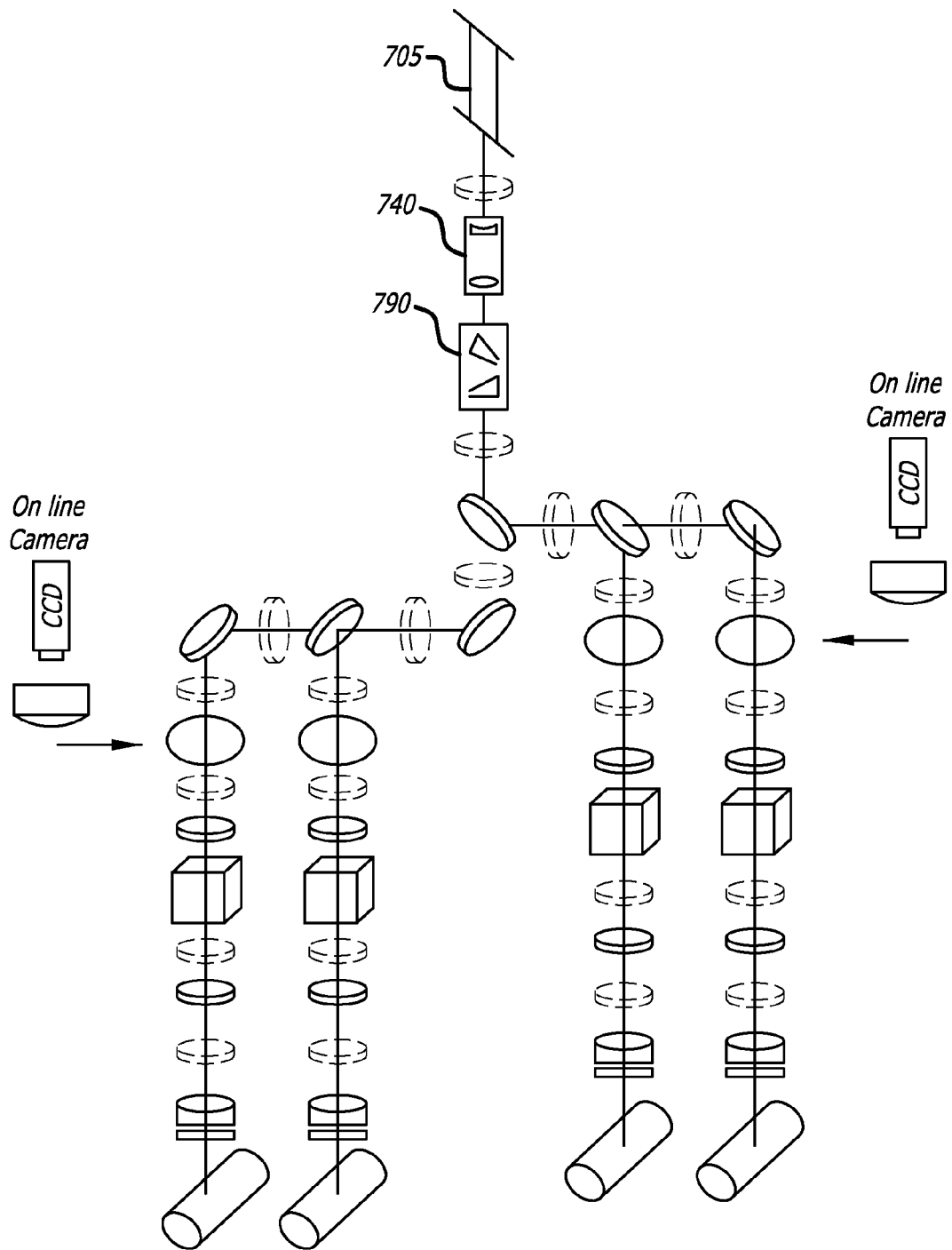
FIG. 9A is a schematic design of an alternative embodiment of the optical layout of FIG. 8 showing the insertion of an optical element such as an anamorphic prism pairs after the beam expander in order to correct beam circularity and/or astigmatism in the laser beam caused by the laser.

FIG. 9A depicts another embodiment of an optical layout using anamorphic prism pairs inserted into the optical path directly after the beam expander to correct circularity, beam shifting and possibly astigmatism caused by the laser. Occasionally, defects in either the design of optical components or their manufacture result in less than optimal optical performance. Such less than optimal optical performance sometimes results in induced astigmatism in the laser beam. This can also occur if the optics of the laser source are also not exactly spherical. One skilled in the art will understand that while this embodiment uses an anamorphic prism pair, other optical devices or elements, such as a cylinder lens, may also be used.

In this embodiment, laser light from laser source 705 is transmitted through beam expander 740. A pair of anamorphic prisms 790 is inserted into the optical path after the beam expander 740 to correct for astigmatism in the laser beam caused by the laser. One example of a prism pair that may be used is model PS870 made by ThorLabs.

Figure 9B:
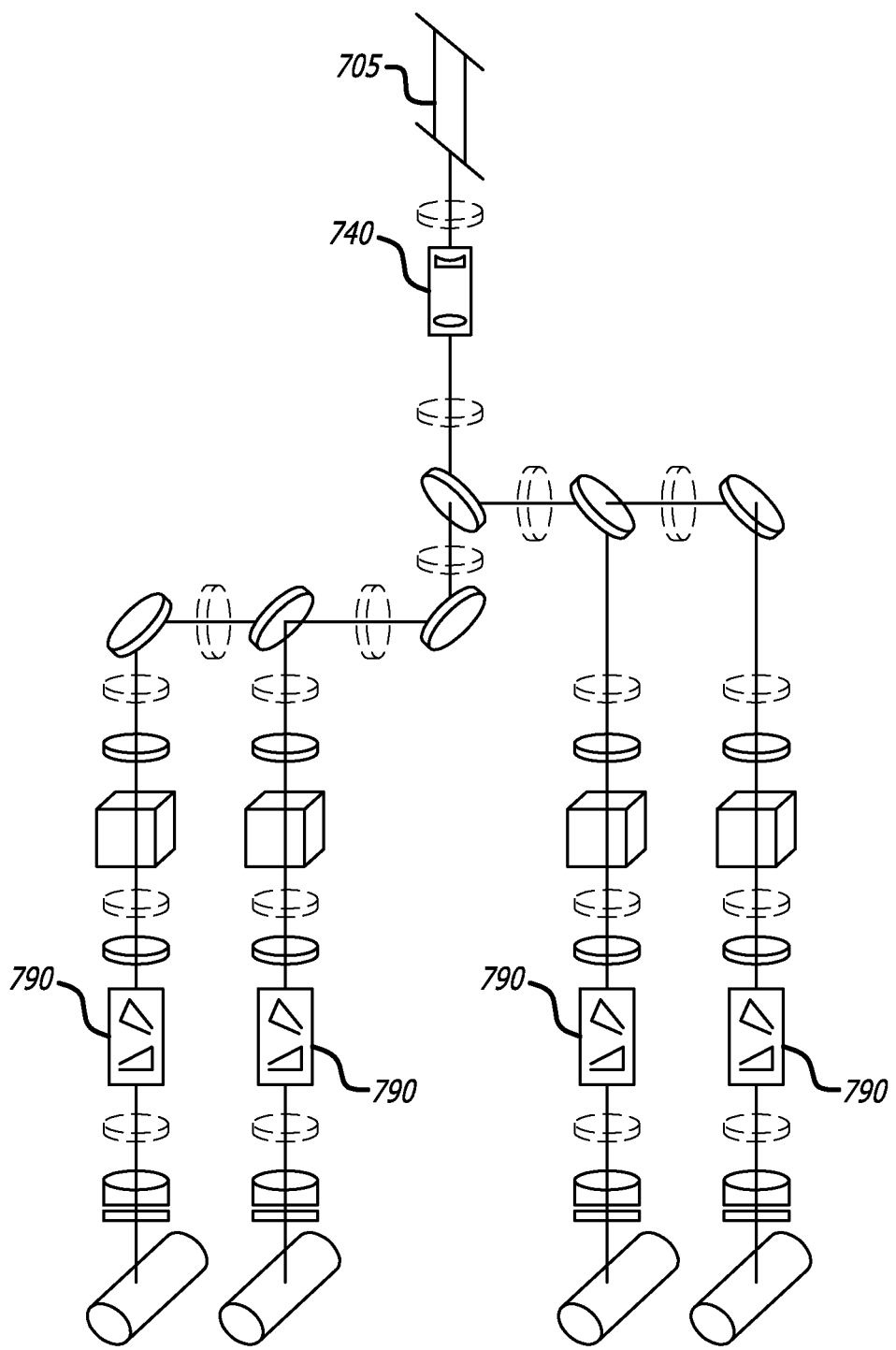
FIG. 9B is a schematic design of an alternative embodiment of the optical layout of FIG. 8 depicting the insertion of anamorphic prism pairs within each individual laser beams to correct astigmatism caused by both the laser and the optical elements in the optical path.

FIG. 9B shows an alternative embodiment of the optical design of FIG. 8 wherein circularity, beam splitting and astigmatism that are caused not only by the laser, but as well imperfections in other optical components in the optical path can be corrected by insertion of anamorphic prism pairs 790 into the end of the optical path. This arrangement allows for individual correction of the astigmatism in each of the arms of the laser cutting setup.

The various embodiments of the present invention provide a multiple beam laser system for use in cutting stents and other pieces where precise control of the cutting beam with acceptable power level is required. Such a system also allows efficient use of pico-second lasers or femto-second lasers which are relatively slow compared to traditional lasers systems that utilize Nd:YAG or fiber lasers. Use of such an optical system as set forth in FIG. 3 makes the use of pico-second lasers or femto-second lasers feasible for scaled up manufacturing of medical device products. The advantages of such a system are that power level, polarization status and spot size, and even beam astigmatism, of each individual laser beam of the multiple beam system can be individually controlled. The optical design of the laser system of the various embodiments described above ensure that an efficient and high-quality laser cut is made in the work product.

The embodiments of the present invention are improvements over previous developed multiple beam laser systems in that circular polarization is introduced to the laser beam after the beam transmits and reflects from all polarization sensitive optics in the optical path. As a result, the cutting laser beam is maximally circularly polarized rather than elliptically or linearly polarized, which improves the cutting quality and efficiency for a multi-directional cutting pattern. In addition, each beam is individually controlled to deliver the desired power level and spot size.

Referring now to FIG. 10, there is a graphical depiction of an embodiment of an automated manufacturing process for producing stents that is designed to cooperate with the multi-beam laser system of FIGS. 3 and 5-9B above. It will be immediately understood, however, that the stent manufacturing system set forth in FIG. 10 is equally applicable to laser cutting systems of 1, 2, 3, or even more beams, and is not limited to the multiple beam laser system described with regard to FIG. 3 et al.

Step 800 of the automated process of FIG. 10 includes a laser source for providing a beam of laser light that will be used to cut a stent pattern into a stent tube. This laser source may be a traditional laser such as an Nd:YAG or fiber laser. However, the greatest benefit of the present invention maybe realized for pico-second and femto-second lasers that exhibit significantly longer processing times than traditional lasers. The longer processing times and high cost associated with pico-second and femto-second lasers make it impractical to operate these lasers at less than full capacity.

As set forth with reference to FIG. 3, the laser beam is split into multiple beams at step 820 to further improve the efficiency of the laser cutting process because the pico-second laser cutting speeds are relatively slow by traditional standards. By splitting the beam, a single laser source may be utilized to cut multiple stents at the same time. The importance of this beam splitting process is key, because it improves overall efficiency while maintaining the integrity and efficacy of the split laser beam.

However, once the laser beams are split, even using the apparatus and systems described herein with reference to at least FIG. 3, the individual characteristics of each laser cutting beam may be different, resulting in the potential for slight differences in the efficiency and quality of the stent pattern that is cut using the individual beam. Accordingly, it is desirable to provide traceability information that is linked to each individual beam, rather than to the laser source alone. One embodiment of an identification means is described in more detail below.

After the laser beam is split into multiple beams in step 820, it may be directed toward raw tubing where the laser beam is used to cut a stent pattern into the tubing to produce a stent. Various steps may be involved in laser cutting the stent, and are dependent upon the design requirements of each cutting system and product to be produced.

In one embodiment, for example, multiple pass laser cuts or ablations may be used to cut the stent from the tubing. Multiple passes may be used to improve the edge quality of the cut stent and to make beam splitting viable by ensuring the stent can be fully fabricated with a laser beam that has relatively less power than conventional laser beams. At this point in the process, it is advantageous to produce some sort of identification means that will link each stent cut to the individual characteristics of the laser beam responsible for the cut. The identification mark may include a barcode or some other code or other machine-readable marker that is related to information about the laser source, the split laser beam, raw tubing material, and/or stent pattern. The information may also be linked to other processing information such as a manufacturing time stamp. All of this information may be further linked to other information stored in a computer memory or other media, such as a lot history record. This information may include, for example, the operator name, environmental conditions, and the like. It will be appreciated that the purpose of this identifier is to provide a means for tracing the history of stent manufacturing.

After the laser beam has been split into individual beams and focused corresponding work pieces (raw tubing), a first pass using the laser beam to cut at least part way through the tubing to cut a pattern into the stent is performed at step 822. At this point, the stent may also be marked with a barcode in step 824, with the stent cutting completed in steps 826 and 828.

Where needed, multiple passes of the laser, such as set forth in steps 826 through 838 may also performed to cut entirely through the tubing to form a stent. This process allows for partial cutting through the thickness of the stent tube with each pass of the laser. Alternatively, different portions of a stent pattern may be cut during each pass of a process using multiple passes of the laser to cut an entire stent pattern into the tube.

For example, in step 826, at least a portion of the pattern is cut into the tubing to a depth that is less than the wall thickness of the tubing. At this time, a lot identifier, which may be, for example, a bar code or other character or number, or some combination of both, can be cut into the surface of the tube to provide for identification and manufacturing tracking of the finished stent. In step 826, the tube surface may be cut in such a manner as to allow for a break link layer, the break link layer for maintaining the structural integrity of the stent while the entire pattern is being cut, and which will ultimately be cut away when the stent is finished.

The laser cutting process is repeated, possible for many repetitions, in steps 828-830, until just the wall thickness of the tube is reduced to a thickness that may be cut away using one more cutting pass by the laser, as indicated by steps 832-834. Finally, the stent pattern is completed in steps 836-838.

The stents output from each laser beam are placed into a separate batch, as indicated in step 850. It should be understood that since the laser beams are separate, it is possible for each batch of stents to have stents formed from different raw materials or with different stent patterns. For example, 15-mm length medium pattern stents may be produced in Batch #1 of step 850 simultaneously with a 30-mm small pattern stent in Batch #2 of step 850.

Control over the specific stent pattern and configuration is enabled through the individual motion control systems of the individual laser beams. These systems are separate from the laser source. Alternatively, a single motion control system may be used to control the motion of multiple cutting pieces that are being cut by separate laser beams. In such an embodiment, multiple cutting pieces will be cut with the same stent pattern to promote the most efficient use of the system. The identifiers, such as bar codes, attached to each stent ensure that the stents remain separate as they progress through subsequent process steps. Alternatively, the lot history information described above could also be included on batch packaging.

In step 870, the batches of stents are sorted into individual stents for individual packaging. Sorting techniques for reducing batches to individual stents can be designed by one skilled in the art. In one embodiment, for example, such a sorting technique includes a hopper table that spreads a batch of stents over an area and empties into a funnel shape or convergent recess that outputs single stents. Batches may be manually or automatically conveyed from the laser cutting process to this sorting process. Automated conveyance may be accomplished by equipment that includes a batch container placed under the stents as they are cut. When the stent is formed, it drops into the batched container. When a predetermined number of stents have been cut by the laser and then moved into the batch container, which can be determined through use of either a vision recognition system or weight measurement, the batch container may be conveyed by a belt or linkage system to the batch sorting mechanism.

Before entering the batch sorting mechanism, it may be desirable to have the stent undergo an ultrasonic cleaning process. The ultrasonic cleaning process may occur within the batch container, or the batch container may empty into a second specialized ultrasonic cleaning bath. The ultrasonic cleaning bath may subsequently be emptied automatically or manually into a sieve or heat drying process to make the stents ready for sorting. The dried stent batch may then be conveyed to the sorting mechanism for sorting in accordance with step 870.

In one embodiment, in parallel to the batch sorting process 870, a vial feeding mechanism may be used in step 890 to provide vial containers that are capable of holding a single stent. This parallel sorting process and conveyance of vial containers is important to automation of the entire process as it ensures that individual vial containers and individual stents arrive in the process simultaneously. After the stents have been individually sorted, they are conveyed to an imaging device at step 900 that is operated in combination with a computer processor to detect and transfer information provided on the unique identifier attached to each stent to a memory of the computer. Such information may include, for example, as a serial number or barcode as described above. When the information of the unique identifier has been transferred to the computer, the computer, operating under the control of suitable programming commands embodied in software or hardware, performs a write command that sends the information to a laser marking system in step 920 that is in physical communication with the vial feeding mechanism.

As the vials are individually conveyed in parallel with the individual stents, they pass by the laser marking system and are marked in step 920 with the information that is communicated by the computer. For example, as an individual stent is monitored by the imaging device in step 900, the device may detect the unique identifier mark, such as a bar code, and then send a signal to the computer that, in turn, sends a signal to the laser marking system commanding the laser marking system to mark a vial with the same unique identifier. In this manner, a vial having the appropriate identifier information is created and as the stent and vial come off of their respective conveyors, they are able to be matched in step 940. In this manner, the individual manufacturing history may be traced with reference to the identification information marked onto the vial holding the stent.

In an alternative embodiment, the vial may be marked with a different identifier based on a conversion command that is executed in accordance with software commands stored in the computer's memory. For example, this converted command may result in an identifier that takes into account both the laser cutting lot history information from the original identifier and also links the individual stent to information related to the ultrasonic cleaning and sorting processes. This provides a mechanism for automatically preparing a lot history record that traces each manufacturing step associated with formation of the final stent.

In step 940, the sorted stents and marked vials are matched according to the identifying information included on the stent and vial. Such matching may occur either manually, or may be done by an automated system. Since the conveyance systems for the individual stents and individual vials may be set up in parallel, they serve as input streams to the matching equipment. Thus, computer controlled matching machine may automatically place a stent in each vial. If necessary, a further identification step could be used to read the identifier on the stent and on the laser-marked vial just prior to packaging the stent in the vial to ensure that the proper stent is placed within the proper vial.

After the individual stents are stored within the marked vials, the vials may be conveyed individually or in batches in step 950 according to their lot history to an electrochemical polishing step 960. The polishing process may be conducted either manually or automatically, and is envisioned as providing for tracing the process applied to each single part. Moreover, this process may also include non-electrically based polishing processes such as acid etches and passivation steps.

The polishing process may be performed in the same manufacturing line as the laser cutting and packaging steps, or it may alternatively be performed in a separate manufacturing line. In any case, stent traceability is maintained during the polishing process by use of the marked vials.

In one embodiment of the present invention, the unique identifier information attached to stent may be removed during the electrochemical polishing step 960. This may be accomplished by polishing away the marked label, removing a sufficient depth of material to remove the marking. Alternatively, where the unique identifier is in the shape of a tag or other physical device attached to the stent, the polishing process may remove the attachment of the tag or device and allow separation of the tag or device from the stent. After removal of the identification tag or device or laser marking on the surface of the stent, the marked vial serves as the identification label that allows the stent information to trace back to the original laser cutting process.

Following polishing of the stent, the stents are replaced in their respective storage vials and are conveyed either individually or in batches based on the stent size and pattern in step 980. The finished stents are either stored for further processing or are packaged.

Figure 11:
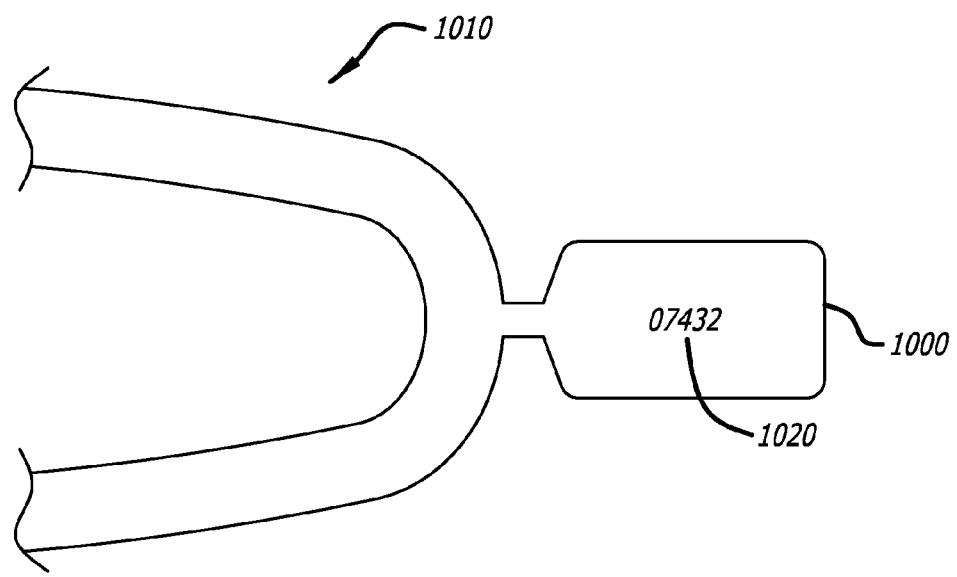
FIG. 11 is a top plan view of an embodiment of a marking tag cut by a laser as part of a stent pattern cut from a tube.

FIG. 11 illustrates one embodiment of an identification tag which is formed on a stent during the laser cutting process, such as in step 824, described above. In this embodiment, a small tab 1000 is included as part of the stent pattern, such as, for example, attached to a stent strut 1010. Those skilled in the art will immediately appreciate that the tab may be attached to stent in any of a variety of locations, as determined by the design of the stent pattern and to promote efficient manufacture of the stent.

The tab 1000 includes an identification mark 1020, such as a serialized number or other information, that is cut on the tab, preferably by the laser-cutting beam, when the stent pattern is cut into the tube. The identification mark 1020 may take some form other than a serial number, such as, for example, a barcode or some other machine-readable marker that is contains or represents information about selected portions of the stent manufacturing process, such as, for example, the laser source, the individual laser beam used to cut the stent, raw tubing material, particular stent pattern, electrochemical polishing and the like.

As described above, the information may also be linked to other processing information, such a manufacturing time stamp, or other information stored in a lot history record such as the operator name, environmental conditions, and the like. The tab 1000 of this embodiment may be removed during a post-processing step, such as after the vial and stent have been matched in step 940, either through a manual process or through an automatic process such as an acid etch or the like.

The various embodiments of the automated process described improve the efficiency of the stent manufacturing process by maximizing the throughput of the laser cutting process while maintaining unit control with additional marking and identification techniques. Moreover, since batching of stent manufacture is used there is minimal downtime associated with product line change-outs and maintenance, since the lasers and electro-polishing processes do not need to be retooled or reprogrammed for each batch of stents. It should be understood that the various embodiments of the above-described automated stent cutting process are applicable to the manufacturer of any stent pattern using any available stent material.

It will be apparent from the foregoing that the present invention provides a new and improved method and apparatus for direct laser cutting of metal stents enabling greater precision, reliability, structural integrity and overall quality, minimal creation of heat affected zones (HAZ), without burrs, slag or other imperfections which might otherwise hamper stent integrity and performance while providing for highly efficient use of a laser cutting system. Moreover, various embodiments of the present invention also provide for tracking the manufacturing history of a cut stent. Other modifications and improvements may be made without departing from the scope of the invention. Accordingly, it is not intended that the invention be limited, except as by the appended claims.

We claim:

1. A method for manufacturing stents using a multiple beam cutting process comprising:
splitting a laser beam into at least two laser beams;
cutting a stent pattern into a tube using one of the at least two laser beams;
marking the stent pattern with an identifier;
sorting a batch of stents into individual stents;
reading the identifier on an individual stent;
marking information related to the identifier on a vial; and
placing the individual stent into the marked vial.

2. The method of claim 1, further comprising:
removing remove the identifier from the stent.

3. The method of claim 2, wherein removing the identifier includes electrochemically polishing the stent to remove the identifier.

4. The method of claim 2, where removing the identifier includes cutting the identifier from the stent.

5. The method of claim 1, wherein reading the identifier on the stent includes:
digitizing the identifier; and
storing the digitized identifier in a memory in operable communication with a processor.

6. The method of claim 5, wherein marking information related to the identifier on a vial includes:
reading the digitized identifier of a stent from the memory;
associating the digitized identifier with data related to the manufacture of the stent;
marking selected data related to the manufacture of the stent on the vial.

\* \* \* \* \*